(12) United States Patent
Tanaka (10) Patent No.: US 10,094,780 B2
(45) Date of Patent: Oct. 9, 2018

(54) IMAGING APPARATUS AND METHOD

(71) Applicant: FUJIFILM Corporation, Tokyo (JP)

(72) Inventor: Yasutake Tanaka, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/429,172

(22) Filed: Feb. 10, 2017

(65) Prior Publication Data

US 2017/0241909 A1 Aug. 24, 2017

(30) Foreign Application Priority Data

Feb. 18, 2016 (JP) ................. 2016-028615

(51) Int. Cl.
| | |
|---|---|
| *G01N 21/64* | (2006.01) |
| *G01N 27/447* | (2006.01) |
| *G01N 21/55* | (2014.01) |

(52) U.S. Cl.
CPC ......... *G01N 21/6402* (2013.01); *G01N 21/55* (2013.01); *G01N 21/6456* (2013.01); *G01N 27/44721* (2013.01); *G01N 2021/6419* (2013.01); *G01N 2201/1042* (2013.01)

(58) Field of Classification Search
CPC .... G01N 21/6402; G03B 42/02; H04N 1/028; H04N 1/04
See application file for complete search history.

(56) References Cited

U.S. PATENT DOCUMENTS

2015/0264257 A1 9/2015 Tanaka et al.

FOREIGN PATENT DOCUMENTS

| JP | 2002-156714 | | 5/2002 |
|---|---|---|---|
| JP | 2002156714 A | * | 5/2002 |
| JP | 2015-177250 | | 10/2015 |

OTHER PUBLICATIONS

"Search Report of Europe Counterpart Application", dated May 23, 2017, p. 1-p. 9.

\* cited by examiner

*Primary Examiner* — Mark R Gaworecki
(74) *Attorney, Agent, or Firm* — JCIPRNET (57) ABSTRACT

A subject-to-be-examined support unit that supports a subject to be examined, a light source unit that outputs light entering the subject-to-be-examined support unit from a side opposite to a side by which a sample is supported, a fluorescent plate that is illuminated with the light that has been output from the light source unit and passed through the subject-to-be-examined support unit and the sample, and emits fluorescence, a photomultiplier that detects fluorescence that has been emitted from the fluorescent plate and passed through the subject-to-be-examined support unit and the sample, and a plate support unit that supports the fluorescent plate are provided. The plate support unit is structured in such a manner that a distance between the subject-to-be-examined support unit and the fluorescent plate is changeable by moving the fluorescent plate in a direction closer to the subject-to-be-examined support unit and in a direction away therefrom.

18 Claims, 7 Drawing Sheets

| MEASUREMENT MODE | HEIGHT | GAIN | VOLTAGE VALUE | ND FILTER | SHADING CORRECTION DATA |
|---|---|---|---|---|---|
| IMAGE MEASUREMENT MODE | H1 | G1 | V1 | NOT USED | CORRECTION DATA 1 |
| DENSITY MEASUREMENT MODE | H2 | G2 | V2 | USED | CORRECTION DATA 2 |

IMAGING APPARATUS AND METHOD

CROSS-REFERENCE TO RELATED APPLICATION

The present application claims priority under 35 U.S.C. § 119 to Japanese Patent Application No. 2016-028615, filed on Feb. 18, 2016. The above application is hereby expressly incorporated by reference, in its entirety, into the present application.

BACKGROUND

The present disclosure relates to an imaging apparatus and method for imaging a transmission image of a subject to be examined by detecting light that has passed through the subject to be examined.

Conventionally, an imaging apparatus that images a transmission image of a subject to be examined set on a subject-to-be-examined support unit made of glass or the like has been proposed (please refer to Japanese Unexamined Patent Publication No. 2002-156714 (Patent Document 1) and Japanese Unexamined Patent Publication No. 2015-177250 (Patent Document 2)).

For example, in the imaging apparatus disclosed in Patent Document 1, a fluorescent plate is placed on a subject to be examined set on a subject-to-be-examined support unit. Then, the subject-to-be-examined support unit is illuminated with excitation light from a side opposite to a side on which the subject to be examined is set, and the fluorescent plate is illuminated with the excitation light that has passed through the subject-to-be-examined support unit and the subject to be examined. At this time, a part of the excitation light is absorbed by an image recorded on the subject to be examined. Therefore, the fluorescent plate is illuminated with the excitation light the light amount of which is in inverse proportion to the density of the image.

Fluorescence emitted from the fluorescent plate by illumination of the fluorescent plate with excitation light is photoelectrically detected by a detector, such as a photomultiplier, after passing through the subject to be examined and the subject-to-be-examined support unit. At this time, a part of the fluorescence is absorbed by an image recorded on the subject to be examined. Therefore, fluorescence the light amount of which is in inverse proportion to the density of the image is detected by the detector. Further, a transmission image of the subject to be examined is imaged by two-dimensionally scanning the subject to be image with excitation light and by sequentially detecting fluorescence transmitted through the subject to be examined, as described above. The transmission image imaged in this manner has a density gradation about twice as many as the image recorded on the subject to be examined.

SUMMARY

Here, the subject to be examined, which is a subject to be imaged of the transmission image as described above, is for example a gel support body including protein dyed with CBB (Coomassie Brilliant Blue) or dyed with silver after electrophoresis, or the like.

However, in a case where a fluorescent plate is directly placed on a gel dyed in this manner, the fluorescent plate is dyed with a dye, such as CBB. If a transmission image of another subject to be examined is imaged by using the fluorescent plate dyed in this manner, there is a problem that an influence of the dye appears in the image.

In view of the foregoing circumstances, the present disclosure is directed to provide an imaging apparatus and method that can prevent contamination of the fluorescent plate as described above.

A first imaging apparatus of the present disclosure includes a subject-to-be-examined support unit that supports a subject to be examined, a light source unit that outputs light entering the subject-to-be-examined support unit from a side opposite to a side by which the subject to be examined is supported, a plate member that is illuminated with the light that has been output from the light source unit and passed through the subject-to-be-examined support unit and the subject to be examined, and emits fluorescence or reflects light as reflection light, a detector that detects the fluorescence that has been emitted from the plate member and passed through the subject-to-be-examined support unit and the subject to be examined, or the light that has been reflected, as the reflection light, from the plate member and passed through the subject-to-be-examined support unit and the subject to be examined, and a plate support unit that supports the plate member. Further, the plate support unit is structured in such a manner that a distance between the subject-to-be-examined support unit and the plate member is changeable by moving the plate member in a direction closer to the subject-to-be-examined support unit and in a direction away from the subject-to-be-examined support unit.

Further, the first imaging apparatus of the present disclosure may include a drive control unit that changes the distance between the subject-to-be-examined support unit and the plate member by controlling the plate support unit based on information obtained in advance.

Further, in the first imaging apparatus of the present disclosure, the drive control unit may change the distance between the subject-to-be-examined support unit and the plate member by controlling the plate support unit based on information about the subject to be examined.

Further, the first imaging apparatus of the present disclosure may further include a measurement mode control unit that controls in such a manner that an image measurement mode, in which an image signal of the subject to be examined is generated based on a signal detected by the detector, and a density measurement mode, in which an optical density value of the subject to be examined is calculated based on the signal detected by the detector, are switchable. Further, the drive control unit may make the distance between the subject-to-be-examined support unit and the plate member in the density measurement mode narrower than the distance in the image measurement mode by controlling the plate support unit.

A second imaging apparatus of the present disclosure includes a subject-to-be-examined support unit that supports a subject to be examined, a light source unit that outputs light entering the subject-to-be-examined support unit from a side opposite to a side by which the subject to be examined is supported, a plate member that is illuminated with the light that has been output from the light source unit and passed through the subject-to-be-examined support unit and the subject to be examined, and emits fluorescence or reflects light as reflection light, a detector that detects the fluorescence that has been emitted from the plate member and passed through the subject-to-be-examined support unit and the subject to be examined, or the light that has been reflected, as the reflection light, from the plate member and passed through the subject-to-be-examined support unit and the subject to be examined, and a plate support unit that supports the plate member. Further, the plate support unit is structured in such a manner that a setting state of the plate support unit is changeable, and also has a shape that can change a distance between the subject-to-be-examined support unit and the plate member by changing the setting state.

Further, the second imaging apparatus of the present disclosure may include a notification unit that notifies, based on information obtained in advance, the setting state of the plate support unit to be set.

Further, in the second imaging apparatus of the present disclosure, the notification unit may notify, based on information about the subject to be examined, the setting state of the plate support unit to be set.

Further, the second imaging apparatus of the present disclosure may further include a measurement mode control unit that controls in such a manner that an image measurement mode, in which an image signal of the subject to be examined is generated based on a signal detected by the detector, and a density measurement mode, in which an optical density value of the subject to be examined is calculated based on the signal detected by the detector, are switchable. Further, the notification unit may notify the setting state of the plate support unit that makes the distance between the subject-to-be-examined support unit and the plate member in the density measurement mode narrower than the distance in the image measurement mode.

A third imaging apparatus of the present disclosure includes a subject-to-be-examined support unit that supports a subject to be examined, a light source unit that outputs light entering the subject-to-be-examined support unit from a side opposite to a side by which the subject to be examined is supported, a plate member that is illuminated with the light that has been output from the light source unit and passed through the subject-to-be-examined support unit and the subject to be examined, and emits fluorescence or reflects light as reflection light, a detector that detects the fluorescence that has been emitted from the plate member and passed through the subject-to-be-examined support unit and the subject to be examined, or the light that has been reflected, as the reflection light, from the plate member and passed through the subject-to-be-examined support unit and the subject to be examined, and a plate support unit that supports the plate member. Further, the plate support unit is structured in such a manner to be replaceable and also structured in such a manner that a distance between the subject-to-be-examined support unit and the plate member is changeable by replacing the plate support unit.

Further, the third imaging apparatus of the present disclosure may include a notification unit that notifies, based on information obtained in advance, the kind of the plate support unit to be set.

Further, in the third imaging apparatus, the notification unit may notify, based on information about the subject to be examined, the kind of the plate support unit to be set.

Further, the third imaging apparatus of the present disclosure may further include a measurement mode control unit that controls in such a manner that an image measurement mode, in which an image signal of the subject to be examined is generated based on a signal detected by the detector, and a density measurement mode, in which an optical density value of the subject to be examined is calculated based on the signal detected by the detector, are switchable. Further, the notification unit notifies the kind of the plate support unit that makes the distance between the subject-to-be-examined support unit and the plate member in the density measurement mode narrower than the distance in the image measurement mode.

Further, the first through third imaging apparatuses of the present disclosure may include an imaging control unit that changes an imaging condition based on the distance between the subject-to-be-examined support unit and the plate member.

Further, the first through third imaging apparatuses of the present disclosure may further include a correction unit that performs correction processing on an image signal of the subject to be examined generated based on a signal detected by the detector. Further, the correction unit may have correction data based on the distance between the subject-to-be-examined support unit and the plate member.

Further, in the first through third imaging apparatuses of the present disclosure, the correction unit may perform shading correction on an image signal of the subject to be examined.

Further, the first through third imaging apparatuses of the present disclosure may include a density measurement unit that calculates an optical density value of the subject to be examined based on a signal detected by the detector.

Further, in the first through third imaging apparatuses of the present disclosure, a frame member may be provided on a surface of the plate member opposite to a surface of the plate member illuminated with the light, and the frame member extending in the direction of the surface opposite to the surface illuminated with the light.

A first imaging method of the present disclosure includes the steps of illuminating a subject to be examined supported on a subject-to-be-examined support unit with light from a side supported by the subject-to-be-examined support unit, illuminating a plate member with the light that has passed through the subject-to-be-examined support unit and the subject to be examined, and detecting fluorescence that has been emitted from the plate member by illumination of the plate member with the light and passed through the subject-to-be-examined support unit and the subject to be examined, or the light that has been reflected, as the reflection light, from the plate member by illumination of the plate member with the light and passed through the subject-to-be-examined support unit and the subject to be examined. Further, a plate support unit that supports the plate member is provided, and a distance between the subject-to-be-examined support unit and the plate member is changeable.

According to the first imaging apparatus of the present disclosure, a plate support unit that supports a plate member that emits fluorescence or reflects light as reflection light by illumination with light that has passed through a subject to be examined is provided. Therefore, it is possible to arrange the subject to be examined and the plate member with a space therebetween. Accordingly, it is possible to prevent contamination of the plate member caused by direct contact between the subject to be examined and the plate member. Further, a distance between the subject-to-be-examined support unit and the plate member is changeable by moving the plate member in a direction closer to the subject-to-be-examined support unit and in a direction away from the subject-to-be-examined support unit. Therefore, it is possible to appropriately adjust the distance between the subject to be examined and the plate member, for example, based on a measurement mode (an image measurement mode and a density measurement mode), the thickness of the subject to be examined or the like. The measurement mode will be described later in detail.

According to the second imaging apparatus of the present disclosure, a plate support unit that supports a plate member that emits fluorescence or reflects light as reflection light by illumination with light that has passed through a subject to be examined is provided. Therefore, it is possible to arrange the subject to be examined and the plate member with a space therebetween. Accordingly, it is possible to prevent contamination of the plate member caused by direct contact between the subject to be examined and the plate member. Further, the plate support unit is structured in such a manner that a setting state of the plate support unit is changeable, and the plate support unit also has a shape that can change a distance between the subject-to-be-examined support unit and the plate member by changing the setting state. Therefore, it is possible to appropriately adjust the distance between the subject to be examined and the plate member by changing the setting state of the plate support unit, for example, based on a measurement mode, the thickness of the subject to be examined or the like.

According to the third imaging apparatus of the present disclosure, a plate support unit that supports a plate member that emits fluorescence or reflects light as reflection light by illumination with light that has passed through a subject to be examined is provided. Therefore, it is possible to arrange the subject to be examined and the plate member with a space therebetween. Accordingly, it is possible to prevent contamination of the plate member caused by direct contact between the subject to be examined and the plate member. Further, the plate support unit is structured in such a manner to be replaceable and also structured in such a manner that a distance between the subject-to-be-examined support unit and the plate member is changeable by replacing the plate support unit. Therefore, it is possible to appropriately adjust the distance between the subject to be examined and the plate member by replacing the plate support unit, for example, based on a measurement mode, the thickness of the subject to be examined or the like.

Regarding the imaging method of the present disclosure, effects similar to the first through third imaging apparatuses of the present disclosure are obtainable.

BRIEF DESCRIPTION OF THE DRAWINGS

FIG. 4 is a diagram illustrating an example of a correspondence table between measurement modes and the height of a fluorescent plate or the like;

FIG. 6 is diagram illustrating an example of a correspondence table between sample information and the height of a fluorescent plate or the like;

DETAILED DESCRIPTION OF THE PREFERRED EMBODIMENTS

Figure 1:
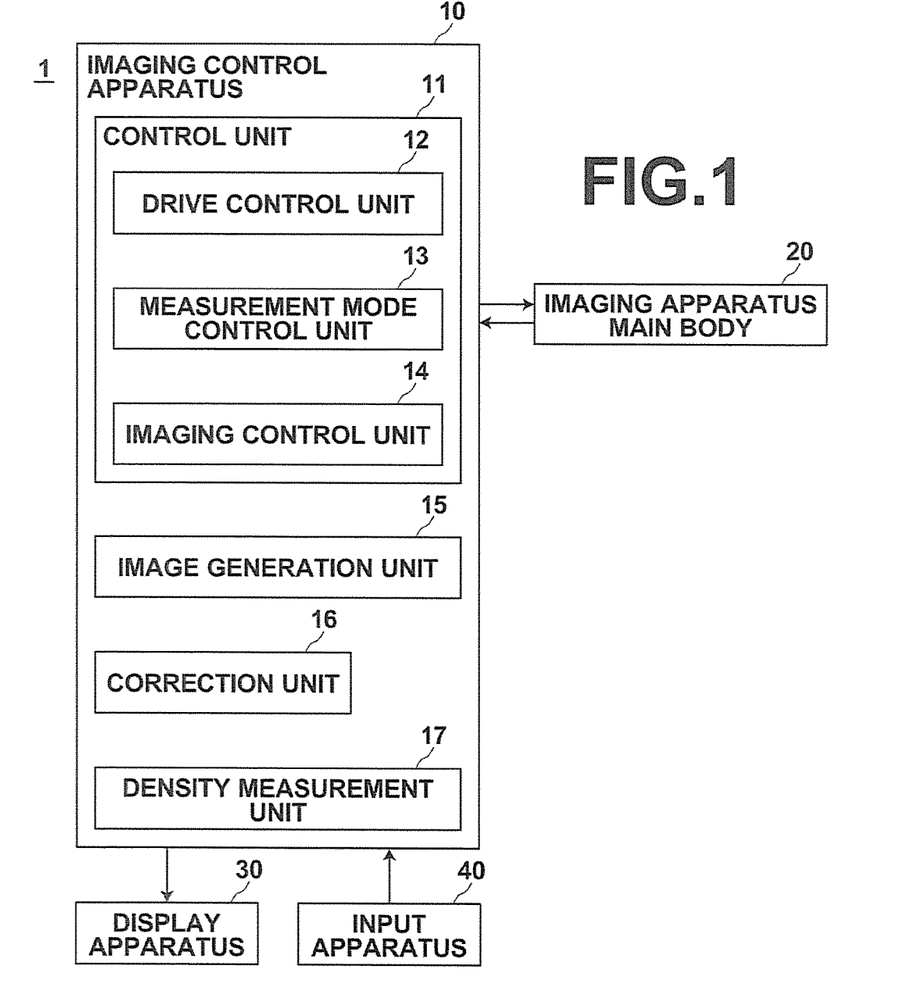
FIG. 1 is a schematic block diagram illustrating the configuration of a first embodiment of an imaging apparatus of the present disclosure.

Next, a first embodiment of an imaging apparatus of the present disclosure will be described in detail with reference to drawings. FIG. 1 is a schematic block diagram illustrating the configuration of an imaging apparatus 1 of the present embodiment.

The imaging apparatus 1 of the present embodiment includes an imaging control apparatus 10, an imaging apparatus main body 20, a display apparatus 30 and an input apparatus 40, as illustrated in FIG. 1.

The imaging control apparatus 10 is configured by a computer including a CPU (Central Processing Unit), a memory, a hard disk and the like, which configure a control unit 11, an image generation unit 15, a correction unit 16 and a density measurement unit 17, illustrated in FIG. 1. These units will be described later in detail.

The imaging apparatus main body 20, the display apparatus 30 and the input apparatus 40 are connected to the imaging control apparatus 10. The display apparatus 30 is configured by a display device, such as a liquid crystal display. The input apparatus 40 is configured by an input device, such as a keyboard and a mouse. A touch panel, which functions both as the display apparatus 30 and as the input apparatus 40, may be adopted.

Figure 2:
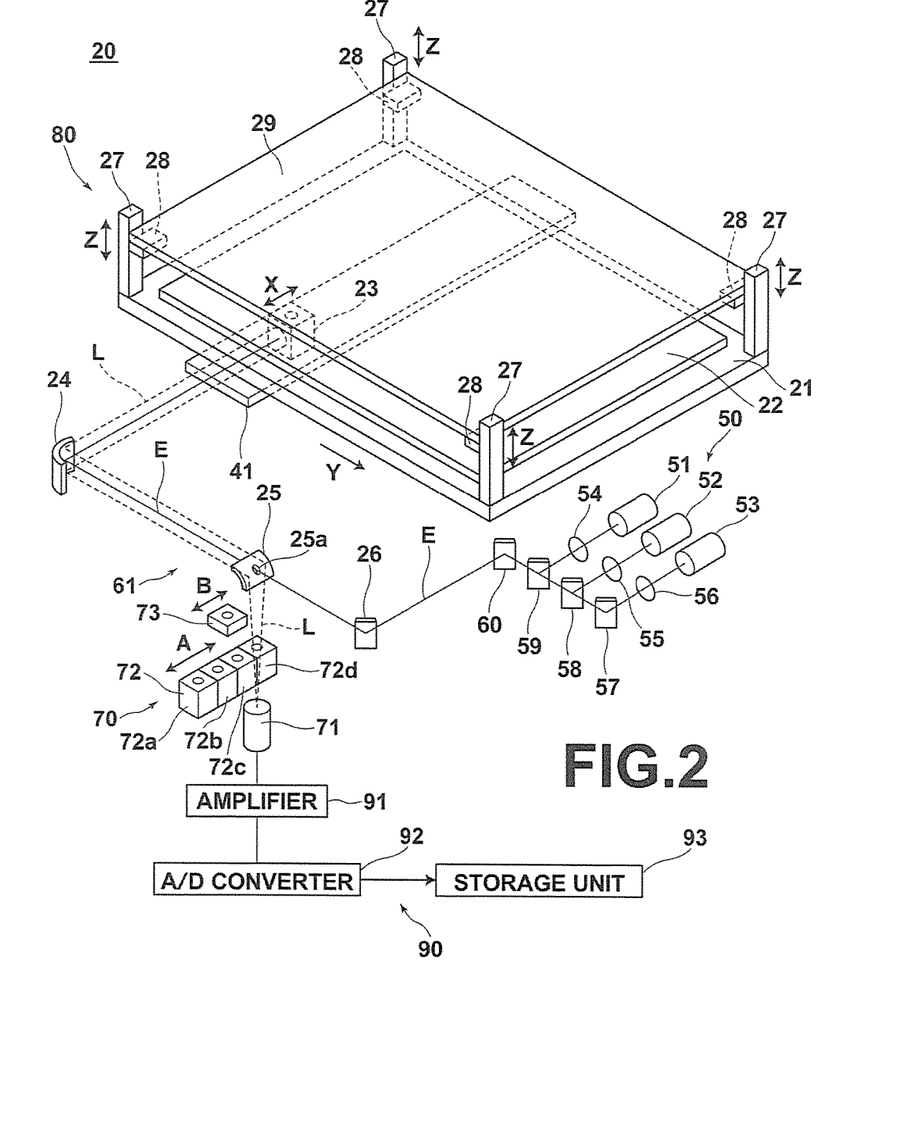
FIG. 2 is a schematic diagram illustrating the configuration of the main body of an imaging apparatus.

FIG. 2 is a schematic diagram illustrating the configuration of the imaging apparatus main body 20. The imaging apparatus main body 20 includes a subject-to-be-examined support unit 21, a light source unit 50, a fluorescent plate 29, a plate support unit 80, a detection unit 70, an optical system 61 and a circuit unit 90, as illustrated in FIG. 2.

A sample 22 corresponding to the subject to be examined is set on the subject-to-be-examined support unit 21, and the subject-to-be-examined support unit 21 supports the sample 22. The subject-to-be-examined support unit 21 is configured by a plate-shaped member, and formed of material transparent to the wavelengths of excitation light E output from the light source unit 50 and fluorescence L emitted from the fluorescent plate 29. Specifically, the subject-to-be-examined support unit 21 is, for example, made of transparent resin, glass or the like. In the present embodiment, the fluorescent plate 29 corresponds to the plate member of the present disclosure.

The sample 22 is, for example, a gel support body including protein dyed with a CBB or dyed with silver. A band pattern obtained by electrophoresis of the dyed protein has been formed in the sample 22. This band pattern is optically read by the imaging apparatus main body 20. Here, the sample 20 is not limited to this sample, and any sample may be used as long as an image pattern like the aforementioned band pattern is formed by absorption of a part of fluorescence emitted from the fluorescent plate 29.

Further, the present disclosure has characteristics in the imaging method used during imaging of a transmission image of the sample 22, as described above. However, the imaging apparatus 1 of the present embodiment is configured in such a manner that imaging of, for example, a fluorescent image of a gel support body including a DNA (deoxyribonucleic acid) fragment that has been fluorescence-labeled and also separated by electrophoresis and a fluorescent image based on fluorescence emitted from a storable phosphor sheet on which a radiographic image has been recorded is also possible besides imaging of the transmission image. Here, in cases where the aforementioned fluorescent images of the fluorescence-labeled gel support body and the storable phosphor sheet are imaged, the fluorescent plate 29 is not set. Here, imaging of a transmission image of the sample 22 will mainly be described.

A plate support unit 80 that supports the fluorescent plate 29 is provided on a surface of the subject-to-be-examined support unit 21 on which the sample 22 is set. The plate support unit 80 includes support posts 27 provided at four corners of the subject-to-be-examined support unit 21 and a movement member 28 attached to each of the support posts 27 movably in the longitudinal direction (Z direction) of each of the support posts 27. As illustrated in FIG. 2, four corners of the fluorescent plate 29 are mounted on the movement members 28 of the support posts 27, respectively. Accordingly, the sample 22 and the fluorescent plate 29 are arranged with a space therebetween.

Figure 3:
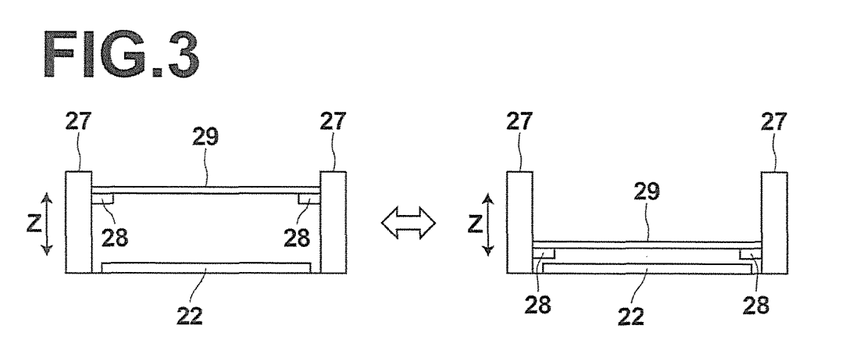
FIG. 3 is a schematic diagram illustrating the movement of movement members and a fluorescent plate.

Further, the fluorescent plate 29 moves in Z direction by synchronous movement of the four movement members 28 with respect to Z direction. FIG. 3 is a schematic diagram illustrating the movement of the movement members 28 and the fluorescent plate 29. The fluorescent plate 29 moves in a direction closer to the subject-to-be-examined support unit 21 (the right section of FIG. 3) and in a direction away from the subject-to-be-examined support unit 21 (the left section of FIG. 3) by movement of the four movement members 28 in Z direction. Specifically, the fluorescent plate 29 moves in a direction closer to the sample 22 set on the subject-to-be-examined support unit 21 and in a direction away from the sample 22. The distance between the fluorescent plate 29 and the sample 22 is adjusted by moving the fluorescent plate 29 in Z direction in this manner. A method for adjusting the distance between the fluorescent plate 29 and the sample 22 will be described later in detail.

The light source unit 50 includes a first excitation light source 51 that outputs excitation light E with the center wavelength of 473 nm, a second excitation light source 52 that outputs excitation light E with the center wavelength of 532 nm, and a third excitation light source 53 that outputs excitation light E with the center wavelength of 640 nm. In the present embodiment, all of the first excitation light source 51, the second excitation light source 52 and the third excitation light source 53 are configured by laser light sources, but not limited to the laser sources. For example, LED (light emitting diode) light sources may be used.

Further, the light source unit 50 includes collimator lenses 54, 55, 56 for collimating excitation light E output from the first through third excitation light sources 51 through 53 and mirrors 57, 60 and first and second dichroic mirrors 58, 59 for guiding excitation light E to the optical system 61.

The first dichroic mirror 58 transmits excitation light E of 640 nm and reflects light with the wavelength of 532 nm. Further, the second dichroic mirror 59 transmits light with a wavelength of 532 MD or longer and reflects light with the wavelength of 473 nm.

Excitation light E output from the first excitation light source 51 is collimated by the collimator lens 54. After then, the direction of the collimated light is changed by 90 degrees by being reflected by the second dichroic mirror 59, and the reflected light enters the mirror 60.

Further, excitation light E output from the second excitation light source 52 is collimated by the collimator lens 55. After then, the direction of the collimated light is changed by 90 degrees by being reflected by the first dichroic mirror 58, and the reflected light passes through the second dichroic mirror 59 and enters the mirror 60.

Excitation light E output from the third excitation light source 53 is collimated by the collimator lens 56. After then, the collimated light is reflected by the mirror 57, and passes through the first dichroic mirror 58 and the second dichroic mirror 59, and enters the mirror 60.

The first through third excitation light sources 51 through 53 are used switchably for each of imaging of a transmission image of the sample 22, imaging of a fluorescent image of a fluorescence-labeled gel support body, and imaging of a fluorescent image of a storable phosphor sheet.

Excitation light E that has entered the mirror 60 is reflected by the mirror 60, and enters a mirror 26 in the optical system 61.

The optical system 61 includes the aforementioned mirror 26, a mirror 25 with a hole, and a concave mirror 24. The mirror 25 with a hole splits excitation light E and fluorescence L, which has been emitted from the fluorescent plate 29. The mirror 25 with a hole is configured by a concave mirror having a hole 25a at its central part.

Excitation light E that has been reflected by the mirror 60 in the light source unit 50 and entered the mirror 26 in the optical system 61 is reflected by the mirror 26 in the optical system 61. The reflected light passes through the hole 25a of the mirror 25 with the hole, and enters the concave mirror 24. The reflected light is reflected by the concave mirror 24, and enters the optical head 23.

The optical head 23 includes a concave mirror and an aspheric lens, which are not illustrated. Further, excitation light E that has entered the optical head 23 is reflected, by the concave mirror, toward the subject-to-be-examined support unit 21 and the sample 22, and condensed, by the aspheric lens, onto the sample 22 set on the subject-to-be-examined support unit 21.

The optical head 23 is attached to an optical head support substrate 41 movably in the longitudinal direction (X direction) of the optical head support substrate 41. Further, the optical head support substrate 41 is provided in such a manner to be movable in a direction (Y direction) orthogonal to the longitudinal direction of the optical head support substrate 41 by a movement mechanism, which is not illustrated.

The entire surface of the sample 22 is scanned with excitation light E by moving the optical head support substrate 41 in Y direction, and also by moving the optical head 23 in X direction at each position of the optical head support substrate 41 for Y direction.

Excitation light E that has illuminated the sample 22 passes through the sample 22, and illuminates the fluorescent plate 29. The fluorescent plate 29 emits fluorescence L by illumination with excitation light E. As the fluorescent plate 29, for example, a fluorescent plate made of an acrylic denatured vinyl chloride resin containing a fluorescent dye may be used. However, the fluorescent plate 29 is not limited to this, and other known fluorescent plates may be used.

Fluorescence L emitted from an excitation light illumination position on the fluorescent plate 29 passes through the sample 22 and the subject-to-be-examined support unit 21, and enters the optical head 23.

Fluorescence L that has entered the optical head 23 is condensed by the aspheric lens in the optical head 23, and enters the concave mirror in the optical head 23. Fluorescence L is reflected by the concave mirror to the same side as the optical path of excitation light E, and collimated, and enters the concave mirror 24 in the optical system 61.

The fluorescence that has entered the concave mirror 24 is reflected by the concave mirror 24, and enters the mirror 25 with a hole. Fluorescence L that has entered the mirror 25 with a hole is reflected by the mirror 25 with a hole toward the detection unit 70.

The detection unit 70 includes a photomultiplier 71, corresponding to a detector, a filter unit 72 and an ND (Neutral Density) filter 73. Fluorescence L reflected by the mirror 25 with a hole enters the filter unit 72, and light of unneeded wavelengths is cut. The remaining light enters the photomultiplier 71, and is photoelectrically detected.

The filter unit 72 includes a first filter member 72a, a second filter member 72b, a third filter member 72c and a fourth filter member 72d. The filter unit 72 is configured movably in the direction of arrow A illustrated in FIG. 2 by a motor or the like, which is not illustrated.

The first filter member 72a is used in a case where a transmission image or a fluorescent image of a fluorescence-labeled gel support body, as described above, is imaged by using the first excitation light source 51. The first filter member 72a cuts excitation light E with the wavelength of 473 nm, and transmits light with a wavelength longer than 473 nm.

The second filter member 72b is used in a case where a fluorescent image of a fluorescence-labeled gel support body is imaged by using the second excitation light source 52. The second filter member 72b cuts light with the wavelength of 532 nm, and transmits light with a wavelength longer than 532 nm.

The third filter member 72c is used in a case where a fluorescent image of a fluorescence-labeled gel support body is imaged by using the third excitation light source 53. The third filter member 72c cuts light with the wavelength of 640 nm, and transmits light with a wavelength longer than 640 nm.

The fourth filter member 72d is used in a case where a fluorescent image of a storable phosphor sheet is imaged by using the third excitation light source 53. The fourth filter member 72d transmits only light in the wavelength range of stimulated emission light emitted from stimulable phosphor of the storable phosphor sheet, and cuts light with the wavelength of 640 nm.

The first through fourth filter members 72a through 72d are arranged at the front surface of the photomultiplier 71 selectively based on the subject to be imaged, and the photomultiplier 71 photoelectrically detects only light to be detected.

The ND filter 73 is configured movably in the direction of arrow B illustrated in FIG. 2 by a motor or the like, which is not illustrated. The ND filter 73 is arranged on an optical path between the mirror 25 with a hole and the filter unit 72 or moved out from the optical path by movement in the direction of arrow B.

A circuit unit 90 includes an amplifier 91, an A/D converter 92 and a storage unit 93. The amplifier 91 amplifies an image signal photoelectrically detected by the photomultiplier 71. The amplifier 91 is configured in such a manner that a gain is changeable. The gain of the amplifier 91 is changed based on a distance between the sample 22 and the fluorescent plate 29, in other words, the height of the fluorescent plate 29.

The A/D converter 92 converts an analog image signal that has been output from the photomultiplier 71 and amplified by the amplifier 91 into a digital image signal. Further, the storage unit 93 is configured by a semiconductor memory or the like, and stores the digital image signal output from the A/D converter 92. The digital image signal stored in the storage unit 93 is output to the imaging control apparatus 10.

Back to FIG. 1, the imaging control apparatus 10 includes the control unit 11, the image generation unit 15, the correction unit 16 and the density measurement unit 17, as described above.

The control unit 11 controls the whole imaging apparatus 1. Specifically, the control unit 11 includes a drive control unit 12 that controls drive of the movement members 28 of the plate support unit 80, a measurement mode control unit 13 that controls switching between an image measurement mode and a density measurement mode, as will be described later, and an imaging control unit 14.

The drive control unit 12 changes a distance between the sample 22 and the fluorescent plate 29 by moving the four movement members 28, in other words, changes the height of the fluorescent plate 29. Specifically, the drive control unit 12 changes the distance between the subject-to-be-examined support unit 21 and the fluorescent plate 29 based on the measurement mode (the image measurement mode or the density measurement mode) controlled by the measurement mode control unit 13 or sample information representing the kind of the sample 22.

The measurement mode control unit 13 switches the image measurement mode and the density measurement mode from each other. In the image measurement mode, the measurement mode control unit 13 generates, based on a digital image signal output from the imaging apparatus main body 20, a whole image signal of an image representing a band pattern on the sample 22 by controlling the image generation unit 15. Meanwhile, in the density measurement mode, the measurement mode control unit 13 calculates, based on the digital image signal output from the imaging apparatus main body 20, the optical density value of the sample 22 by controlling the density measurement unit 17.

Here, changing a distance between the sample 22 and the fluorescent plate 29 will be described in detail. As described above, the drive control unit 12 determines the height of the fluorescent plate 29 based on the measurement mode or the sample information, and controls drive of each movement member 28 so that the height of the fluorescent plate 29 becomes the determined height. First, a case where the height of the fluorescent plate 29 is changed based on the measurement mode will be described.

Figure 4:
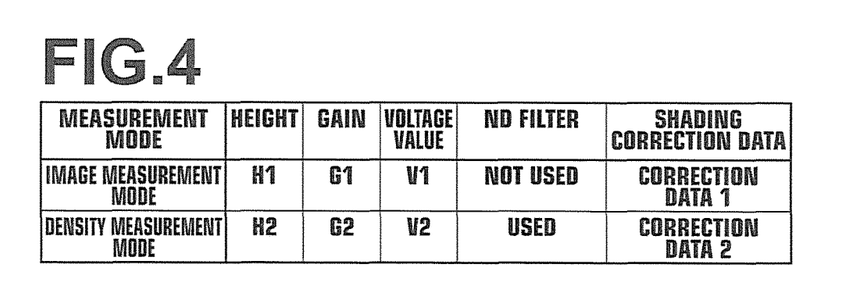

Specifically, a correspondence table between measurement modes and the height of the fluorescent plate 29, as illustrated in FIG. 4, has been set in advance in the drive control unit 12. The measurement mode is set by an input by a user by using the input apparatus 40. The drive control unit 12 determines, based on the input measurement mode, the height of the fluorescent plate 29 with reference the table illustrated in FIG. 4.

For example, in a case where a user has set an image measurement mode by an input, the drive control unit 12 determines the height of the fluorescent plate 29 as H1, and sets the height to H1 by adjusting the height of the fluorescent plate 29 by controlling the drive of each movement member 28 of the plate support unit 80. Further, for example, in a case where a user has set a density measurement mode by an input, the drive control unit 12 determines the height of the fluorescent plate 29 as H2, and sets the height to H2 by adjusting the height of the fluorescent plate 29 by controlling the drive of each movement member 28 of the plate support unit 80.

The height of the fluorescent plate 29 is adjusted based on the measurement mode, as described above, because a more accurate density value is often required in the density measurement mode in which the density value of the sample 22 is calculated, and therefore more accurate imaging is required. Hence, it is desirable that the height of the fluorescent plate 29 is lower. In contrast, in the image measurement mode in which an image of the sample 22 is displayed on the display apparatus 30, priority is given to imaging of a thicker sample 22. Therefore, it is desirable that the height of the fluorescent plate 29 is higher. Specifically, the relationship between height H1 of the fluorescent plate 29 in the case where the sample 22 is imaged in the image measurement mode and height H2 of the fluorescent plate 29 in the case where the sample 22 is imaged in the density measurement mode is H1>H2.

Further, the imaging control unit 14 of the control unit 11 changes the imaging condition based on the height of the fluorescent plate 29. Specifically, the imaging control unit 14 changes the gain of the amplifier 91 and the value of voltage applied to the photomultiplier 71.

More specifically, the length of an optical path from the fluorescent plate 29 to the photomultiplier 71 becomes relatively longer as the height of the fluorescent plate 29 becomes higher. Therefore, a smaller image signal is detected by the photomultiplier 71. Hence, the imaging control unit 14 sets the gain of the amplifier 91 and the value of voltage applied to the photomultiplier 71 greater as the height of the fluorescent plate 29 is higher. For example, the imaging control unit 14 sets the gain of the amplifier 91 to 1 times and the value of voltage applied to the photomultiplier 71 to 500 V in a case where the height of the fluorescent plate 29 is 5 mm. The imaging control unit 14 sets the gain of the amplifier 91 to 10 times and the value of voltage applied to the photomultiplier 71 to 800 V in a case where the height of the fluorescent plate 29 is 15 mm. Accordingly, an image signal in a desirable intensity is obtainable.

Further, imaging control unit 14 controls, based on the measurement mode, whether the ND filter 73 is used, as one of imaging conditions. Specifically, the imaging control unit 14 controls in such a manner that the ND filter 73 is moved out from the optical path between the mirror 25 with a hole and the filter unit 72 in the image measurement mode and that the ND filter is arranged on the optical path in the density measurement mode. The ND filter is used in the density measurement mode to prevent failure in accurate measurement of the density, which is caused by remaining electric charges generated by strong fluorescence, in a case where the strong fluorescence has entered the photomultiplier 71.

Next, the image generation unit 15 generates a whole image signal for display, which will be output to the display apparatus 30 and displayed, by performing signal processing on the input digital image signal.

The correction unit 16 performs shading correction on a whole image signal for display generated by the image generation unit 15 and a whole image signal for density measurement generated by the density measurement unit 17. Plural kinds of correction data for shading correction based on the distance between the sample 22 and the fluorescent plate 29 have been set in advance in the correction unit 16. Specifically, correction data 1 and correction data 2 based on the measurement mode, in other words, based on the height of the fluorescent plate 29, as illustrated in FIG. 4, have been set in advance in the correction unit 16. Such correction data based on the height of the fluorescent plate 29 are used, because the generation condition of unevenness in an imaged image changes if the height of the fluorescent plate 29 changes.

Further, the correction unit 16 determines correction data corresponding to the height of the fluorescent plate 29 determined based on the measurement mode, and performs shading correction on the whole image signal by using the correction data.

The whole image signal for display on which shading correction has been performed is output to the display apparatus 30 by the correction unit 11. Further, an image representing a band pattern of the sample 22 is displayed based on the whole image signal for display on the display apparatus 30.

The density measurement unit 17 generates a whole image signal for density measurement by performing signal processing on the input digital image signal. Further, the density measurement unit 17 calculates a density value by performing, on the whole image signal on which shading correction has been performed by using correction data 2 based on the density measurement mode, conversion processing that has been set in advance. A look-up table in which digital image signals and density values are correlated with each other or a function representing a relationship between them has been set in advance in the density measurement unit 17. The density measurement unit 17 calculates the density value by using the look-up table or the function.

The density value measured by the density measurement unit 17 is output to the display apparatus 30 by the control unit 11, and text display, graph display or the like of the density value is performed.

Figure 5:
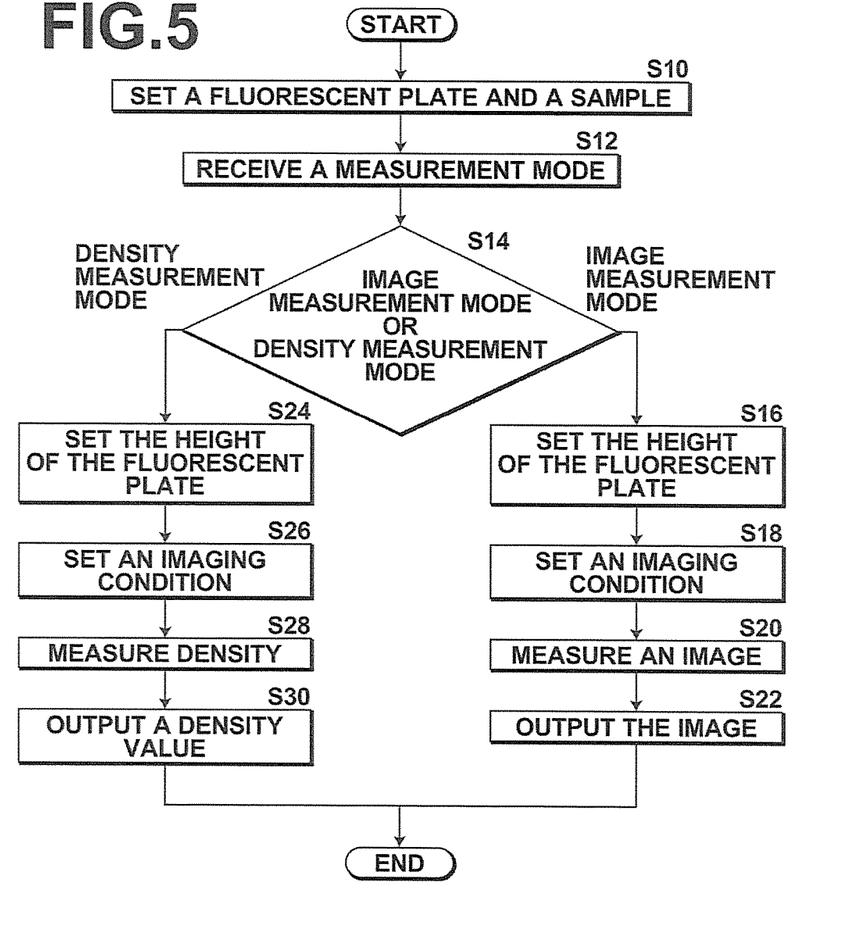
FIG. 5 is a flowchart for explaining an action of the first embodiment of the imaging apparatus of the present disclosure.

Next, the action of the imaging apparatus of the present embodiment will be described with reference to the flowchart illustrated in FIG. 5. Here, a case where the height of the fluorescent plate 29 is changed based on the measurement mode will be described.

First, the sample 22 is set on the subject-to-be-examined support unit 21, and the fluorescent plate 29 is set on each movement member 28 of the plate support unit 80 (S10).

Next, a measurement mode is set by an input by the user using the input apparatus 40. The measurement mode is received by the drive control unit 12 (S12).

In a case where the measurement mode set by the input is an image measurement mode (S14), the height of the fluorescent plate 29 is determined based on the information about the image measurement mode. The drive of the movement members 28 of the plate support unit 80 is controlled, and the height of the fluorescent plate 29 is set (S16). Further, an imaging condition based on the height of the fluorescent plate 29 determined as described above is set (S18). Specifically, the gain of the amplifier 91 and the voltage value of the photomultiplier 71 are set based on the height of the fluorescent plate 29, and the ND filter 73 is moved out from the optical path between the mirror 25 with a hole and the photomultiplier 71.

Further, the control unit 11 controls the imaging apparatus main body 20, and image measurement is performed (S20). Specifically, excitation light E is output from the first excitation light source 51, and the optical head 23 is moved in X direction, and the optical head support substrate 41 is moved in Y direction. Accordingly, the sample 22 and the fluorescent plate 29 are two-dimensionally scanned with excitation light E. Further, fluorescence L that has been emitted from the fluorescent plate 29 by illumination with excitation light E and passed through the sample 22 sequentially enters the optical head 23. Fluorescence L that has entered the optical head 23 is reflected by the mirror 25 with a hole, and passes through the first filer member 72a of the filter unit 72. Further, fluorescence L is detected by the photomultiplier 71.

The image signal detected by the photomultiplier 71 is amplified by the amplifier 91, and converted to a digital image signal by the A/D converter 92. After then, the digital image signal is stored in the storage unit 93.

The digital image signal stored in the storage unit 93 is output to the image generation unit 15, and the image generation unit 15 generates a whole image signal for display by performing signal processing on the input digital image signal. The whole image signal for display generated by the image generation unit 15 is output to the correction unit 16, and the correction unit 16 performs shading correction by using correction data based on the height of the fluorescent plate 29.

Further, the control unit 11 displays, based on the whole image signal for display on which shading correction has been performed, an image of the sample 22 on the display apparatus 30 (S22).

Meanwhile, in a case where the measurement mode set by the input is a density measurement mode (S14), the height of the fluorescent plate 29 is determined based on the information about the density measurement mode. The drive of the movement members 28 of the plate support unit 80 is controlled, and the height of the fluorescent plate 29 is set (S24). Further, an imaging condition based on the height of the fluorescent plate 29 determined as described above is set (S26). Specifically, the gain of the amplifier 91 and the voltage value of the photomultiplier 71 are set based on the height of the fluorescent plate 29, and the ND filter 73 is set on the optical path between the mirror 25 with a hole and the photomultiplier 71.

Further, the control unit 11 controls the imaging apparatus main body 20, and density measurement is performed (S28). Specifically, excitation light E is output from the first excitation light source 51, and the optical head 23 is moved in X direction, and the optical head support substrate 41 is moved in Y direction. Accordingly, the sample 22 and the fluorescent plate 29 are two-dimensionally scanned with excitation light E. Further, fluorescence L that has been emitted from the fluorescent plate 29 by illumination with excitation light E and passed through the sample 22 sequentially enters the optical head 23. Fluorescence L that has entered the optical head 23 is reflected by the mirror 25 with a hole, and passes through the ND filter 73 and the first filer member 72a of the filter unit 72. Further, fluorescence L is detected by the photomultiplier 71.

The image signal detected by the photomultiplier 71 is amplified by the amplifier 91, and converted to a digital image signal by the A/D converter 92. After then, the digital image signal is stored in the storage unit 93.

The digital image signal stored in the storage unit 93 is output to the density measurement unit 17, and the density measurement unit 17 generates a whole image signal for density measurement by performing signal processing on the input digital image signal. The whole image signal for density measurement generated by the density measurement unit 17 is output to the correction unit 16, and the correction unit 16 performs shading correction by using the correction data based on the height of the fluorescent plate 29.

The density measurement unit 17 calculates a density value based on the whole image signal for density measurement on which shading correction has been performed at the correction unit 16.

Further, the control unit 11 performs text display or graph display of the density value calculated by the density measurement unit 17 on the display apparatus 30 (S30).

According to the imaging apparatus 1 of the first embodiment, the plate support 80, which supports the fluorescent plate 29 and also arranges the sample 22 and the fluorescent plate 29 with a space therebetween, is provided. Therefore, it is possible to prevent contamination of the fluorescent plate 29 caused by direct contact between the subject to be examined and the fluorescent plate. Further, since the distance between the sample 22 and the fluorescent plate 29 is changeable by moving the fluorescent plate 29 in a direction closer to the sample 22 and in a direction away from the sample 22, it is possible to appropriately adjust the distance between the sample 22 and the fluorescent plate 29 based on the measurement mode.

Further, since the distance between the sample 22 and the fluorescent plate 29 is automatically changeable, the user's work of changing the distance is not needed.

In the imaging apparatus 1 of the above embodiment, the height of the fluorescent plate 29 was determined based on the measurement mode. Alternatively, the height of the fluorescent plate 29 may be determined based on the sample information, as described already. Next, a case where the height of the fluorescent plate 29 is changed based on the sample information will be described.

Figure 6:
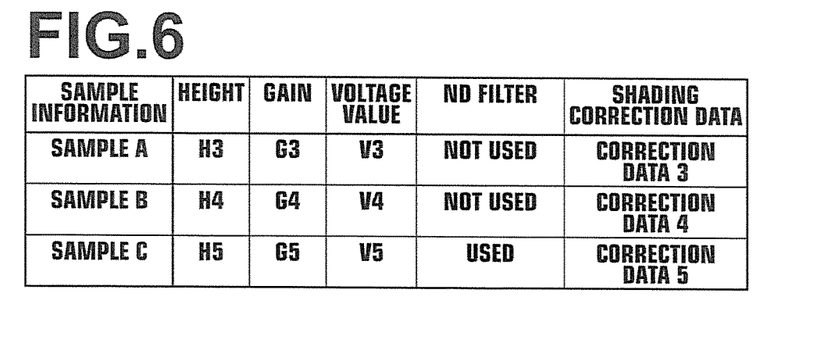

In this case, a correspondence table between sample information and the height of the fluorescent plate 29, as illustrated in FIG. 6, has been set in advance in the drive control unit 12. The sample information is set by an input by the user using the input apparatus 40, and the drive control unit 12 determines, based on the input sample information, the height of the fluorescent plate 29 with reference to the table illustrated in FIG. 6.

For example, in a case where a user has set information about sample A by an input, the drive control unit 12 determines the height of the fluorescent plate 29 as H3, and sets the height to H3 by adjusting the height of the fluorescent plate 29 by controlling the drive of each movement member 28 of the plate support unit 80. Further, for example, in a case where a user has set information about sample B by an input, the drive control unit 12 determines the height of the fluorescent plate 29 as H4, and sets the height to H4 by adjusting the height of the fluorescent plate 29 by controlling the drive of each movement member 28 of the plate support unit 80. In a case where information about sample C has been set by an input, the drive control unit 12 sets the height of the fluorescent plate 29 to H5 also in a similar manner.

The height of the fluorescent plate 29 is adjusted in this manner based on the sample information, because the thickness of the sample 22 (the height from the surface of the subject-to-be-examined support unit 21 on which the sample is set) differs depending on the kind of the sample 22. It is possible to make the intensity of a signal detected by the photomultiplier 71 higher as the fluorescent plate 29 is moved closer to the sample 22 based on the thickness of the sample 22. Accordingly, it is possible to image a high-quality image. Hence, the height of the fluorescent plate 29 is higher as the thickness of the sample is thicker, and the height of the fluorescent plate 29 is lower as the thickness of the sample is thinner.

Figure 7:
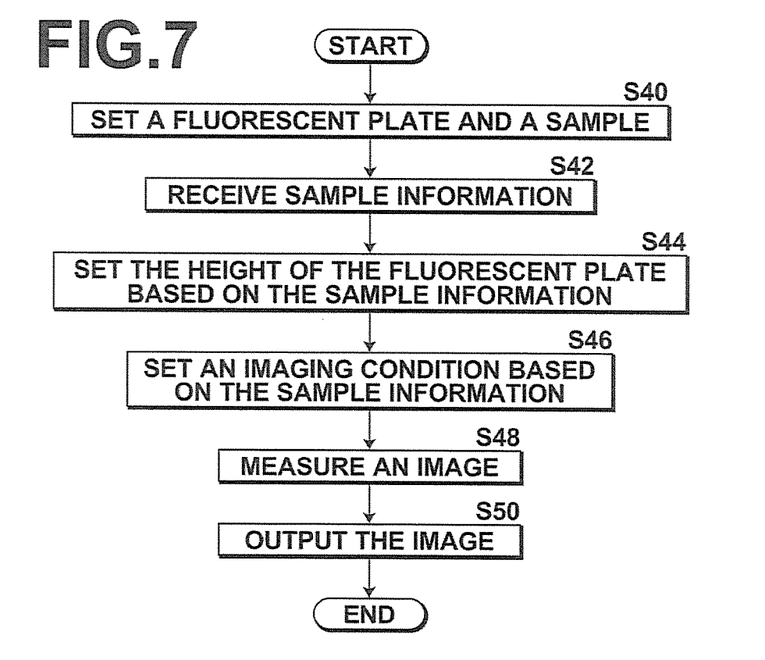
FIG. 7 is a flowchart for explaining another action of the first embodiment of the imaging apparatus of the present disclosure.

Next, the action in a case of changing the height of the fluorescent plate 29 based on sample information will be described with reference to the flowchart illustrated in FIG. 7. Here, a case where image measurement is performed will be described.

First, the sample 22 is set on the subject-to-be-examined support unit 21, and the fluorescent plate 29 is set on each movement member 28 of the plate support unit 80 (S40).

Next, sample information is set by an input by the user using the input apparatus 40. The sample information is received by the drive control unit 12 (S42).

Then, the height of the fluorescent plate 29 is determined based on the sample information set by the input. The drive of the movement members 28 of the plate support unit 80 is controlled, and the height of the fluorescent plate 29 is set (S44). Further, an imaging condition based on the height of the fluorescent plate 29 determined as described above is set (S46). Specifically, the gain of the amplifier 91 and the voltage value of the photomultiplier 71 are set based on the height of the fluorescent plate 29, and the position of the ND filter 73 is controlled. Here, whether the ND filter 73 is to be used is determined based on the intensity of fluorescence L that has been emitted from the fluorescent plate 29 and passed through the sample 22. In a case where the intensity of fluorescence L is high, the ND filter 73 is used to prevent saturation of the image signal.

Further, the control unit 11 controls the imaging apparatus main body 20, and image measurement is performed (S48). Further, an image of the sample 22 is displayed on the display apparatus 30 based on the whole image signal for display on which shading correction has been performed (S50).

In the above descriptions, image measurement was performed. The height of the fluorescent plate 29 and the imaging condition may be changed based on the sample information also in density measurement.

In the imaging apparatus 1 of the above embodiment, the user set the sample information or the measurement mode by the input, and the height of the fluorescent plate 29 was changed based on the information. However, for example, the user may input wrong information about these items, and there is a risk of contact of the fluorescent plate 29 with the sample 22. Therefore, for example, an optical sensor or the like may detect a state in which the fluorescent plate 29 is too close to the sample 22. In a case where the fluorescent plate 29 is too close to the sample 22, the control unit 11 may issue an alert to the user by displaying an error message on the display apparatus 30, turning on a lamp or making warning sound before the fluorescent plate 29 contacts with the sample 22. As the aforementioned optical sensor, for example, a light output unit that outputs laser light and a light receiving unit that receives the laser light may be provided for movement members 28 that diagonally face each other. A state in which the fluorescent plate 29 is too close to the sample 22 may be detected by detecting a state in which no more laser light is received by the light receiving unit.

Alternatively, instead of receiving an input of setting the sample information, the thickness of the sample 22 set on the subject-to-be-examined support unit 21 may be measured directly by laser measurement or the like. Further, the height of the fluorescent plate 29 may be controlled based on the measured thickness.

Next, a second embodiment of the imaging apparatus of the present disclosure will be described. In the imaging apparatus 1 of the first embodiment, the height of the fluorescent plate 29 was automatically adjusted by the plate support unit 80. However, in an imaging apparatus 2 of the second embodiment, a user sets the height of the fluorescent plate 29 manually based on the kind of the sample 22 or the measurement mode.

Figure 8:
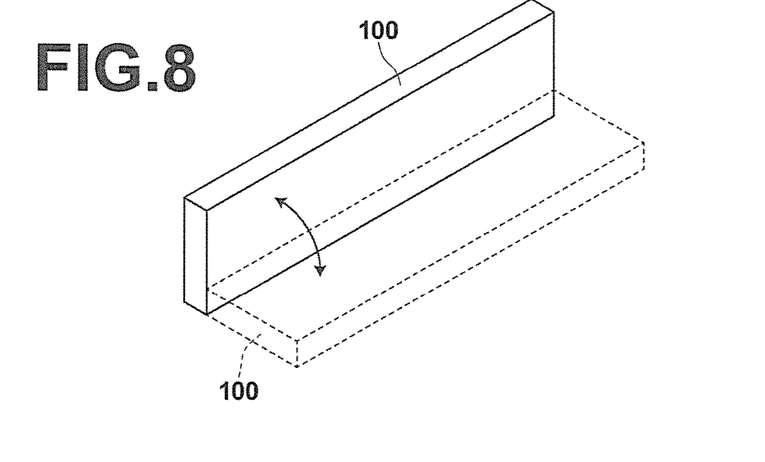
FIG. 8 is a diagram illustrating an example of a plate support unit in a second embodiment of an imaging apparatus of the present disclosure.
Figure 9:
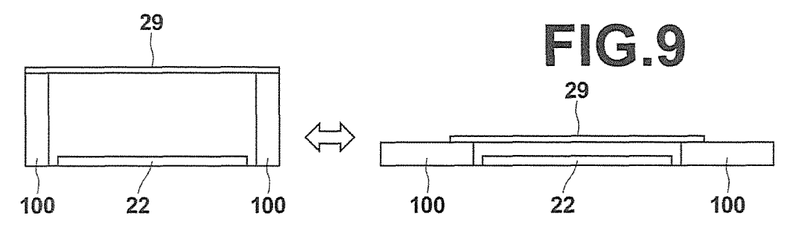
FIG. 9 is a diagram for explaining change in a setting state of the plate support unit in the second embodiment of the imaging apparatus of the present disclosure.

Specifically, the imaging apparatus 2 of the second embodiment includes a set of plate support units 100 formed by rectangular parallelepipeds, as illustrated in FIG. 8. The plate support unit 100 is set at a side edge portion on the subject-to-be-examined support unit 21, and a side edge portion of the fluorescent plate 29 is mounted on the plate support unit 100. As illustrated in FIG. 8 and FIG. 9, the state of setting the plate support unit 100 is manually changed by the user. Accordingly, the distance between the subject-to-be-examined support unit 21 and the fluorescent plate 29 (the height of the fluorescent plate 29) is changed. In other words, the distance between the sample 22 and the fluorescent plate 29 is changed. A left section of FIG. 9 illustrates a state in a case where the plate support unit 100 is set as indicated by a solid line in FIG. 8, and a right section of FIG. 9 illustrates a state in a case where the plate support unit 100 is set as indicated by a broken line in FIG. 8. As illustrated in FIG. 8 and FIG. 9, the state of setting is changed by changing the setting surface of the plate support unit 100, formed by rectangular parallelepiped, on the subject-to-be-examined support unit 21. Accordingly, the height of the fluorescent plate 29 is changed.

Figure 10:
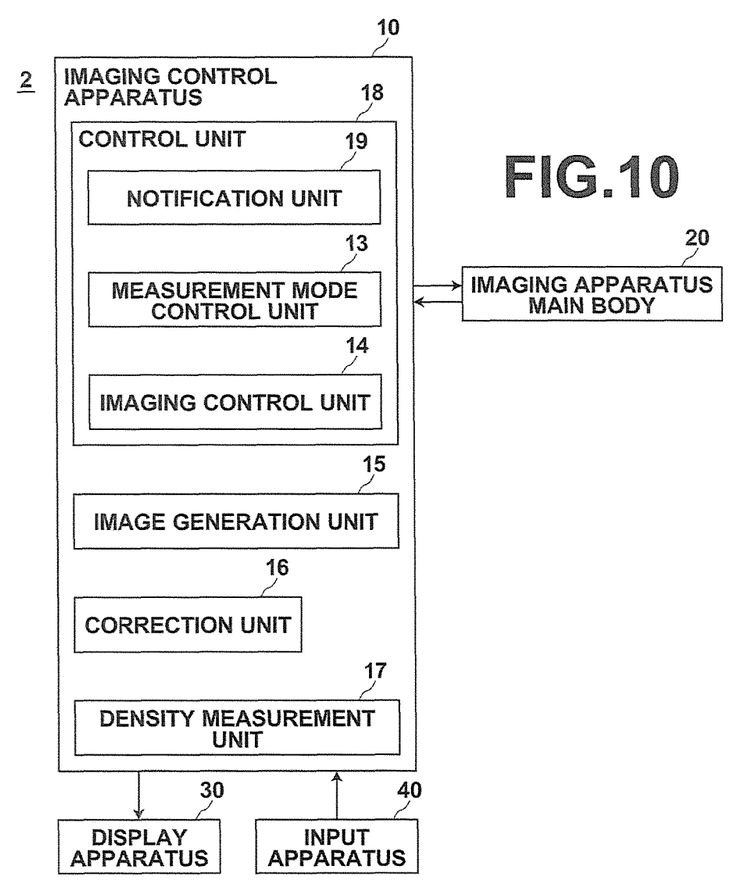
FIG. 10 is a schematic block diagram illustrating the configuration of second and third embodiments of the imaging apparatus of the present disclosure.

Further, in the imaging apparatus 2 of the second embodiment, the aforementioned state of setting the plate support unit 100 is notified to the user. Specifically, in the imaging apparatus 2 of the second embodiment, the control unit 18 includes a notification unit 19, as illustrated in FIG. 10. The other configuration illustrated in FIG. 10 is similar to the imaging apparatus 1 of the first embodiment.

Specifically, the notification unit 19 determines the state of setting the plate support unit 100 based on the sample information or information about the measurement mode set by the input by the user. Further, the notification unit 19 displays an icon of the determined state of setting the plate support unit 100 on the display apparatus 30. As the icon, for example, one of the diagrams illustrated in the left and right sections of FIG. 9 is displayed as the icon. For example, the notification unit 19 displays the diagram in the left section of FIG. 9, as the icon, in a case where the sample information set by the input by the user is information about a relatively thick sample. The notification unit 19 displays the diagram in the right section of FIG. 9, as the icon, in a case where the sample information is information about a relatively thin sample. Alternatively, the notification unit 19 displays the diagram in the left section of FIG. 9, as the icon, in a case where the measurement mode set by the input by the user is an image measurement mode. The notification unit 19 displays the diagram in the right section of FIG. 9, as the icon, in a case where the measurement mode is a density measurement mode. The notification unit 19 displays an icon representing the state of setting in which the distance between the fluorescent plate 29 and the sample 22 is narrower in the density measurement mode.

According to the second imaging apparatus 2 of the second embodiment, the plate support unit 100 that supports the fluorescent plate 29 and also arranges the sample 22 and the fluorescent plate 29 with a space therebetween is provided. Therefore, it is possible to prevent contamination of the fluorescent plate 29 caused by direct contact between the sample 22 and the fluorescent plate 29. Further, the plate support unit 100 is structured in such a manner that the state of setting the plate support unit 100 is changeable, and also the plate support unit 100 has a shape that can change the distance between the sample and the fluorescent plate by changing the state of setting. Therefore, it is possible to appropriately adjust the distance between the sample 22 and the fluorescent plate 29 by changing the state of setting the plate support unit 100 based on the thickness of the sample 22 or the like.

Further, the distance between the sample 22 and the fluorescent plate 29 is changeable just by changing the state of setting the plate support unit 100. Therefore, it is possible to simplify the configuration, compared with the automatic control as in the imaging apparatus 1 of the first embodiment. Hence, reduction in cost is possible.

A case where a user inputs wrong sample information or wrong information about a measurement mode is considered also in the imaging apparatus 2 of the second embodiment in a similar manner to the imaging apparatus 1 of the first embodiment. Therefore, an optical sensor or the like may detect a state in which the fluorescent plate 29 is too close to the sample 22. In a case where the fluorescent plate 29 is too close to the sample 22, an alert may be issued to the user.

Instead of receiving the input of setting the sample information, the thickness of the sample 22 set on the subject-to-be-examined support unit 21 may be directly measured by laser measurement or the like, and an icon based on the measured thickness may be displayed also in the imaging apparatus 2 of the second embodiment in a similar manner to the imaging apparatus 1 of the first embodiment.

Next, a third embodiment of the imaging apparatus of the present disclosure will be described. In the imaging apparatus 2 of the second embodiment, the height of the fluorescent plate 29 was changed by changing the state of setting the plate support unit 100. The imaging apparatus 3 of the third embodiment is structured in such a manner that plural plate support units having different heights from the setting surface on the subject-to-be-examined support unit 21 are replaceable in a case where the plate supports units are set on the subject-to-be-examined support unit 21.

Figure 11:
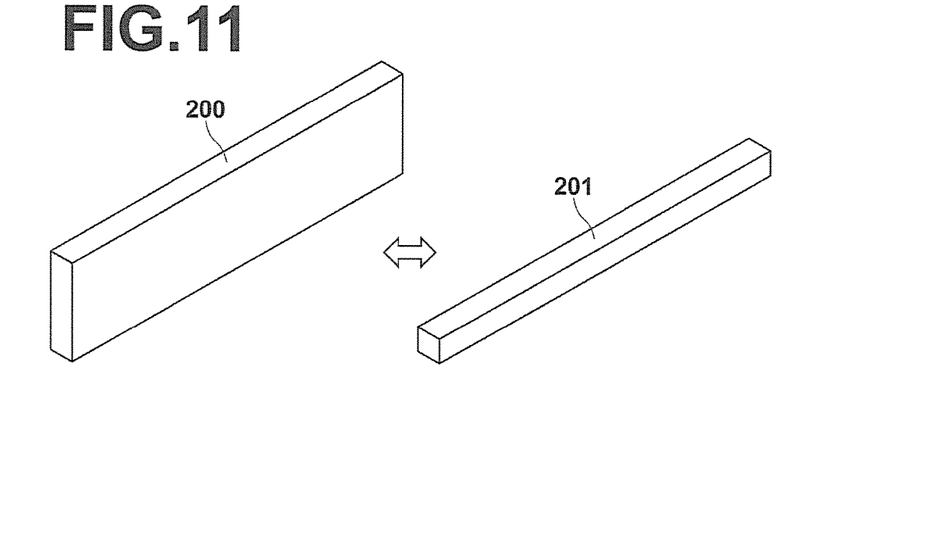
FIG. 11 is a diagram illustrating an example of a plate support unit in the third embodiment of the imaging apparatus of the present disclosure.

Specifically, the imaging apparatus 3 of the third embodiment includes a set of plate support units 200 formed by rectangular parallelepipeds and a set of plate support units 201 formed by square prisms, as illustrated in FIG. 11. The plate support units 200 and the plate support units 201 are members having different heights from the setting surface of the subject-to-be-examined support unit 21 in a case where they are set on the subject-to-be-examined support unit 21.

The plate support units 200, 201 are set at side edge portions on the subject-to-be-examined support unit 21, and side edge portions of the fluorescent plate 29 are mounted on the plate support units 200, 201 in a similar manner to the second embodiment. The plate support units 200 and the plate support units 201 are replaced with each other by the user. Accordingly, the distance between the subject-to-be-examined support unit 21 and the fluorescent plate 29 (the height of the fluorescent plate 29) is changed. In other words, the distance between the sample 22 and the fluorescent plate 29 is changed. In the present embodiment, the two kinds of plate support units 200, 201 are replaceable with each other. However, the plate support units are not limited to two kinds, and three or more kinds of plate support units may be provided. In this case, the height of the fluorescent plate 29 is changeable to three or more levels.

Further, the imaging apparatus 3 of the third embodiment notifies the user of the kind of the plate support unit to be set. The specific structure is similar to the imaging apparatus 2 of the second embodiment, and the control unit 18 includes the notification unit 19 also in the imaging apparatus 3 of the third embodiment.

Specifically, the notification unit 19 in the imaging apparatus 3 of the third embodiment determines the kind of the plate support unit to be set based on the sample information or information about the measurement mode set by the input by the user. Further, the notification unit 19 displays an icon of the determined kind of the plate support unit on the display apparatus 30. As the icon, an icon representing a state in which the fluorescent plate 29 is set on the plate support unit to be set is displayed in a similar manner to the imaging apparatus 2 of the second embodiment. For example, the notification unit 19 displays an icon representing a state in which the fluorescent plate 29 is set on the plate support unit 200, illustrated in FIG. 11, in a case where the sample information set by the input by the user is information about a relatively thick sample. The notification unit 19 displays an icon representing a state in which the fluorescent plate 29 is set on the plate support unit 201, illustrated in FIG. 11, in a case where the sample information is information about a relatively thin sample. Alternatively, the notification unit 19 displays an icon representing a state in which the fluorescent plate 29 is set on the plate support unit 200, illustrated in FIG. 11, in a case where the measurement mode set by the input by the user is the image measurement mode. The notification unit 19 displays an icon representing a state in which the fluorescent plate 29 is set on the plate support unit 201, illustrated in FIG. 11, in a case where the measurement mode is the density measurement mode. The notification unit 19 displays an icon representing the plate support unit 201, which makes the distance between the fluorescent plate 29 and the sample 22 narrower, in the density measurement mode.

According to the third imaging apparatus 3 of the third embodiment, the plate support units 200, 201, which support the fluorescent plate 29 and also arrange the sample 22 and the fluorescent plate 29 with a space therebetween, are provided. Therefore, it is possible to prevent contamination of the fluorescent plate 29 caused by direct contact between the sample 22 and the fluorescent plate 29. Further, the third imaging apparatus 3 is structured in such a manner that the plate support units 200 and the plate support units. 201 are replaceable with each other, and also that the distance between the sample 22 and the fluorescent plate 29 is changeable by replacing these plate support units 200, 201 with each other. Therefore, it is possible to appropriately adjust the distance between the sample 22 and the fluorescent plate 29 by replacing the plate support units 200 and the plate support units 201 with each other based on the thickness of the sample 22 or the like.

Further, since the distance between the sample 22 and the fluorescent plate 29 is changeable just by replacing the plate support units 200 and the plate support units 201 with each other. Therefore, it is possible to simplify the configuration, compared with the automatic control as in the imaging apparatus 1 of the first embodiment. Hence, reduction in cost is possible.

A case where a user inputs wrong sample information or wrong information about a measurement mode may be considered also in the imaging apparatus 3 of the third embodiment in a similar manner to the imaging apparatus 1 of the first embodiment. An optical sensor or the like may detect a state in which the fluorescent plate 29 is too close to the sample 22. In a case where the fluorescent plate 29 is too close to the sample 22, an alert may be issued to the user.

Instead of receiving the input of setting the sample information, the thickness of the sample 22 set on the subject-to-be-examined support unit 21 may be directly measured by laser measurement or the like, and an icon based on the measured thickness may be displayed also in the imaging apparatus 3 of the third embodiment in a similar manner to the imaging apparatus 1 of the first embodiment.

Figure 12:
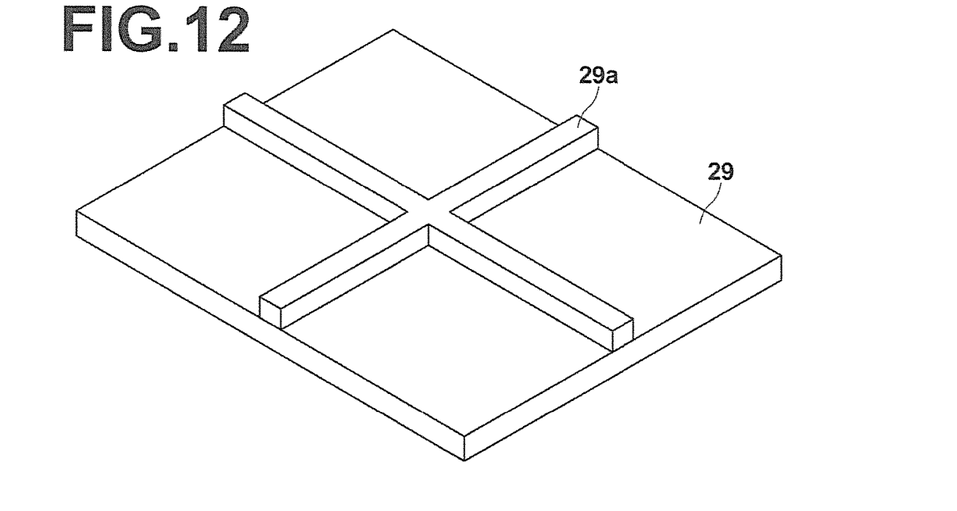
FIG. 12 is a diagram illustrating an example of a fluorescent plate in which a frame member is provided.

In the imaging apparatuses 1 through 3 of the first through third embodiments, a space was provided between the sample 22 and the fluorescent plate 29 by setting the fluorescent plate 29 on the plate support unit. However, in a case where an edge of the fluorescent plate 29 is set on the plate support unit, a central part of the fluorescent plate 29, which is not supported by the plate support unit, may bend by the weight of the fluorescent plate 29 depending on the rigidity of the fluorescent plate 29. Therefore, there is a risk of influencing the intensity of the image signal detected by the photomultiplier 71. Hence, as illustrated in FIG. 12, a frame member 29a may be provided on a surface opposite to a surface of the fluorescent plate 29 illuminated with excitation light E, and the frame member 29a extends in the direction of the surface on which the frame member 29a is provided. The fluorescent plate 29 is reinforced by the frame member 29a, and bending, as described above, is preventable. It is desirable that a cross-shaped frame member 29a is provided, as illustrated in FIG. 12. However, the shape of the frame member 29a is not limited to this shape, and other shapes are adoptable.

Further, in the imaging apparatuses 1 through 3 of the first through third embodiments, a transmission image of the sample 22 was imaged by detecting, by the photomultiplier 71, fluorescence L that had been emitted from the fluorescent plate 29 by illumination with excitation light E and passed through the sample 22. Instead of the fluorescent plate 29, a reflection plate that reflects excitation light E may be used, and a transmission image of the sample 22 may be imaged by detecting, by the photomultiplier 71, reflection light that has been reflected by the reflection plate and passed through the sample 22. The reflection plate does not need to emit fluorescence like the fluorescent plate 29, but should reflect excitation light E. Further, it is desirable that a frame member is provided on a surface opposite to a surface of the reflection plate illuminated with excitation light E, and the frame member extends in the direction of the surface on which the frame member is provided in a similar manner to the case of using the fluorescent plate 29, also in a case where the reflection plate is used.

Further, in the imaging apparatuses 1 through 3 of the first through third embodiments, the photomultiplier 71 was used as the detector. However, the detector is not limited to this, and other devices may be used as long as photoelectric conversion is performed on light. For example, a photo diode, an avalanche photodiode, a CCD (Charge-Coupled Device) sensor, a CMOS (complementary metal oxide semiconductor) sensor or the like may be used.

Further, the imaging apparatuses 1 through 3 of the first through third embodiments include first through third excitation light sources 51 through 53 and first through fourth filter members 72a through 72d, and configured in such a manner that a fluorescent image of a fluorescence-labeled gel support body or a fluorescent image of a storable phosphor sheet is imagable by a combination of these elements. It is desirable that the laser light amount of excitation light used in imaging a fluorescent image of a storable phosphor sheet is less than the laser light amount of excitation light used in imaging a transmission image based on fluorescence emitted from the aforementioned fluorescent plate 29 and a fluorescent image of the fluorescence-labeled gel support body. Normally, stronger fluorescence is excited in the fluorescent plate 29 and the fluorescence label as the laser light amount of excitation light is greater. Therefore, the greater laser light amount is desirable, because the image quality is improved. In contrast, since the storable phosphor sheet adopts destructive readout, a most appropriate laser light amount for the storable phosphor sheet is present.

Specifically, for example in the imaging apparatuses 1 through 3 in the above embodiments, the third excitation light source 53 is used for both of a case where a fluorescent image of the storable phosphor sheet is imaged and a case where a fluorescent image of a fluorescence-labeled gel support body is imaged. The laser light amount in a case of imaging the fluorescent image of the storable phosphor sheet is controlled less than the laser light amount in a case of imaging the fluorescent image of the fluorescence-labeled gel support body. Specifically, for example, the laser light amount in a case of imaging a fluorescent image of the storable phosphor sheet is controlled to $1/10$ of the laser light amount in a case of imaging a fluorescent image of the fluorescence-labeled gel support body.

What is claimed is:

1. An imaging apparatus comprising:
a subject-to-be-examined support unit that supports a subject to be examined;
a light source unit that outputs light entering the subject-to-be-examined support unit from a side opposite to a side by which the subject to be examined is supported;
a plate member that is illuminated with the light that has been output from the light source unit and passed through the subject-to-be-examined support unit and the subject to be examined, and emits fluorescence or reflects light as reflection light;
a detector that detects the fluorescence that has been emitted from the plate member and passed through the subject-to-be-examined support unit and the subject to be examined, or the light that has been reflected, as the reflection light, from the plate member and passed through the subject-to-be-examined support unit and the subject to be examined; and
a plate support unit that supports the plate member,
wherein the plate support unit is structured in such a manner that a distance between the subject-to-be-examined support unit and the plate member is changeable by moving the plate member in a direction closer to the subject-to-be-examined support unit and in a direction away from the subject-to-be-examined support unit.

2. The imaging apparatus, as defined in claim 1, further comprising:
a drive control unit that changes the distance between the subject-to-be-examined support unit and the plate member by controlling the plate support unit based on information obtained in advance.

3. The imaging apparatus, as defined in claim 2, wherein the drive control unit changes the distance between the subject-to-be-examined support unit and the plate member by controlling the plate support unit based on information about the subject to be examined.

4. The imaging apparatus, as defined in claim 2, further comprising:
a measurement mode control unit that controls in such a manner that an image measurement mode, in which an image signal of the subject to be examined is generated based on a signal detected by the detector, and a density measurement mode, in which an optical density value of the subject to be examined is calculated based on the signal detected by the detector, are switchable,
wherein the drive control unit makes the distance between the subject-to-be-examined support unit and the plate member in the density measurement mode narrower than the distance in the image measurement mode by controlling the plate support unit.

5. The imaging apparatus, as defined in claim 1, further comprising:
an imaging control unit that changes an imaging condition based on the distance between the subject-to-be-examined support unit and the plate member.

6. The imaging apparatus, as defined in claim 1, further comprising:
a correction unit that performs correction processing on an image signal of the subject to be examined generated based on a signal detected by the detector,
wherein the correction unit has correction data based on the distance between the subject-to-be-examined support unit and the plate member.

7. The imaging apparatus, as defined in claim 6, wherein the correction unit performs shading correction on an image signal of the subject to be examined.

8. The imaging apparatus, as defined in claim 1, further comprising:
a density measurement unit that calculates an optical density value of the subject to be examined based on a signal detected by the detector.

9. The imaging apparatus, as defined in claim 1, wherein a frame member is provided on a surface of the plate member opposite to a surface of the plate member illuminated with the light, and the frame member extending in the direction of the surface opposite to the surface illuminated with the light.

10. An imaging apparatus comprising:
a subject-to-be-examined support unit that supports a subject to be examined;
a light source unit that outputs light entering the subject-to-be-examined support unit from a side opposite to a side by which the subject to be examined is supported;
a plate member that is illuminated with the light that has been output from the light source unit and passed through the subject-to-be-examined support unit and the subject to be examined, and emits fluorescence or reflects light as reflection light;
a detector that detects the fluorescence that has been emitted from the plate member and passed through the subject-to-be-examined support unit and the subject to be examined, or the light that has been reflected, as the reflection light, from the plate member and passed through the subject-to-be-examined support unit and the subject to be examined; and
a plate support unit that supports the plate member,
wherein the plate support unit is structured in such a manner that a setting state of the plate support unit is changeable, and also has a shape that can change a distance between the subject-to-be-examined support unit and the plate member by changing the setting state.

11. The imaging apparatus, as defined in claim 10, further comprising:
a notification unit that notifies, based on information obtained in advance, the setting state of the plate support unit to be set.

12. The imaging apparatus, as defined in claim 11, wherein the notification unit notifies, based on information about the subject to be examined, the setting state of the plate support unit to be set.

13. The imaging apparatus, as defined in claim 11, further comprising:
a measurement mode control unit that controls in such a manner that an image measurement mode, in which an image signal of the subject to be examined is generated based on a signal detected by the detector, and a density measurement mode, in which an optical density value of the subject to be examined is calculated based on the signal detected by the detector, are switchable,
wherein the notification unit notifies the setting state of the plate support unit that makes the distance between the subject-to-be-examined support unit and the plate member in the density measurement mode narrower than the distance in the image measurement mode.

14. An imaging apparatus comprising:
a subject-to-be-examined support unit that supports a subject to be examined;
a light source unit that outputs light entering the subject-to-be-examined support unit from a side opposite to a side by which the subject to be examined is supported;
a plate member that is illuminated with the light that has been output from the light source unit and passed through the subject-to-be-examined support unit and the subject to be examined, and emits fluorescence or reflects light as reflection light;
a detector that detects the fluorescence that has been emitted from the plate member and passed through the subject-to-be-examined support unit and the subject to be examined, or the light that has been reflected, as the reflection light, from the plate member and passed through the subject-to-be-examined support unit and the subject to be examined; and
a plate support unit that supports the plate member,
wherein the plate support unit is structured in such a manner to be replaceable and also structured in such a manner that a distance between the subject-to-be-examined support unit and the plate member is changeable by replacing the plate support unit.

15. The imaging apparatus, as defined in claim 14, further comprising:
a notification unit that notifies, based on information obtained in advance, the kind of the plate support unit to be set.

16. The imaging apparatus, as defined in claim 15, wherein the notification unit notifies, based on information about the subject to be examined, the kind of the plate support unit to be set.

17. The imaging apparatus, as defined in claim 15, further comprising:
a measurement mode control unit that controls in such a manner that an image measurement mode, in which an image signal of the subject to be examined is generated based on a signal detected by the detector, and a density measurement mode, in which an optical density value of the subject to be examined is calculated based on the signal detected by the detector, are switchable,
wherein the notification unit notifies the kind of the plate support unit that makes the distance between the subject-to-be-examined support unit and the plate member in the density measurement mode narrower than the distance in the image measurement mode.

18. An imaging method comprising the steps of:
illuminating a subject to be examined supported on a subject-to-be-examined support unit with light from a side supported by the subject-to-be-examined support unit;
illuminating a plate member with the light that has passed through the subject-to-be-examined support unit and the subject to be examined; and
detecting fluorescence that has been emitted from the plate member by illumination of the plate member with the light and passed through the subject-to-be-examined support unit and the subject to be examined, or the light that has been reflected, as the reflection light, from the plate member by illumination of the plate member with the light and passed through the subject-to-be-examined support unit and the subject to be examined, wherein a plate support unit that supports the plate member is provided, and a distance between the subject-to-be-examined support unit and the plate member is changeable.

* * * * *